(12) United States Patent
Lamb et al.

(10) Patent No.: US 7,678,758 B2
(45) Date of Patent: Mar. 16, 2010

(54) METHOD FOR ENHANCING T CELL REACTIVITY TOWARD TUMOUR ANTIGENS

(75) Inventors: Jonathan Robert Lamb, Edinburgh (GB); Gerard Francis Hoyne, Canberra (AU)

(73) Assignee: Celldex Therapeutics Ltd., Cambridge (GB)

( * ) Notice: Subject to any disclaimer, the term of this patent is extended or adjusted under 35 U.S.C. 154(b) by 43 days.

(21) Appl. No.: 10/147,329

(22) Filed: May 16, 2002

(65) Prior Publication Data

US 2003/0194804 A1    Oct. 16, 2003

Related U.S. Application Data

(63) Continuation-in-part of application No. PCT/GB00/04391, filed on Nov. 17, 2000.

(30) Foreign Application Priority Data

Nov. 18, 1999    (GB) ................................. 9927328.6

(51) Int. Cl.
    *A61K 38/00*    (2006.01)
(52) U.S. Cl. ......................... 514/2; 424/184.1; 530/350
(58) Field of Classification Search .............. 424/198.1, 424/184.1, 277.1
    See application file for complete search history.

(56) References Cited

U.S. PATENT DOCUMENTS 6,887,475 B1 *   5/2005   Lamb et al. ............... 424/184.1

FOREIGN PATENT DOCUMENTS

| WO | WO 94/07474 | | 4/1994 |
|----|-------------|---|--------|
| WO | WO 96/27610 | | 9/1996 |
| WO | WO 97/27876 | | 9/1997 |
| WO | WO 98/20142 | * | 5/1998 |
| WO | WO 98/45434 | | 10/1998 |
| WO | WO 00/36089 | | 6/2000 |

OTHER PUBLICATIONS

Bodey et al. Failure of cancer vaccines: the significant limitations of this approach to immunotherapy. Anticancer Res. Jul.-Aug. 2000;20(4):2665-76.*
Hemmati-Brivanlou et al. Vertebrate embryonic cells will become nerve cells unless told otherwise. Cell. Jan. 10, 1997;88(1):13-7.*
Hersey P. Impediments to successful immunotherapy. Pharmacol Ther. Feb. 1999;81(2):111-9.*
Medzhitov et al. A human homologue of the Drosophila Toll protein signals activation of adaptive immunity. Nature. Jul. 24, 1997;388(6640):394-7.*
Nawrocki et al. Genetically modified tumour vaccines: an obstacle race to break host tolerance to cancer. Expert Opin Biol Ther. Mar. 2001;1(2):193-204.*
Platsoucas et al. Immune responses to human tumors: development of tumor vaccines. Anticancer Res. May-Jun. 2003;23(3A):1969-96.*
Radtke et al. Notch regulation of lymphocyte development and function. Nat lmmunol. Mar. 2004;5(3):247-53.*
Zlobin et al. Toward the rational design of cell fate modifiers: notch signaling as a target for novel biopharmaceuticals. Curr Pharm Biotechnol. Jul. 2000;1(1):83-106.*
Ostrand-Rosenberg, S. Animal models of tumor immunity, immunotherapy and cancer vaccines. Curr Opin Immunol. Apr. 2004;16(2):143-50.*
Shimizu et al. Mouse jagged1 physically interacts with notch2 and other notch receptors. Assessment by quantitative methods. J Biol Chem. Nov. 12, 1999;274(46):32961-9.*
Beatus et al., "The Notch 3 intracellular domain represses Notch 1-mediated activation through Hairy/Enhancer of split (HES) promoters", Development, vol. 126, pp. 3925-3935, 1999, referred to as XP 002170224.
Bellavia et al, "Constitutive activation of NF-$\kappa B$ and T-cell leukemia/lymphoma in Notch3 transgenic mice", The EMBO Journal, vol. 19, No. 13, pp. 3337-3348, 2000, referred to as XP 002170225.
Hoyne et al., "T-cell regulation of peripheral tolerance and immunity: the potential role for Notch signalling", Immunology, vol. 100, pp. 281-288, 2000, referred to as XP 002170226.
Kevin Fitzgerald, et al., Interchangeability of Caenorhabditis Elegans DSL Proteins and Intrinsic Signalling Activity of their Extracellular Domains In Vivo, Development (1995) vol. 121, p. 4275-4282.
Wei Han, et al., A Soluble Form of Human Delta-Like-1 Inhibits Differentiation of Hematopoietic Progenitor Cells, Blood (2000) vol. 95, No. 5, p. 1616-1625.
Steven A. Rosenberg, et al., A New Approach to the Adoptive Immunotherapy of Cancer with Tumor-Infiltrating Lymphocytes, Science (1986) vol. 233, p. 1318-1321.
Kiyoshi Shimizu, et al., Mouse Jagged1 Physically Interacts With Notch2 and Other Notch receptors, The Journal of Biological Chemistry (1999) vol. 274, No. 46, p. 32961-32969.
John R. Shutter, et al., D114, a Novel Ligand Expressed in Arterial Endothelium, Genes & Development (2000) vol. 14, p. 1313-1318.
Mark Edison, et al., Notch Signaling In The Development Of the Inner Ear: Lessons From Drosophila, PNAS (2000) vol. 97, No. 22, p. 11692-11699.
E-Chiang Lee, et al., The Scabrous Protein Can Act As An Extracellular Antagonist Of Notch Signaling In The Drosophila Wing, Current Biology (2000) vol. 10, No. 15, p. 931-934.
Linheng Li, et al., The Human Homolog Of Rat Jagged1 Expressed By Marrow Stroma Inhibits Differentiation Of 32D Cells Through Interaction With Notch1, Immunity (1998) vol. 8, p. 43-55.
Morgenstern and Land (1990) Nucleic Acids Res. 18 :3587-3596.
Cosset etal. (1995) J. Virol. 69: 7430-7436.
Coffin Rs, et al. (1998) Gene Therapy 5: 718-722.

(Continued)

*Primary Examiner*—Eileen B O Hara
(74) *Attorney, Agent, or Firm*—Frommer Lawrence & Haug LLP; Thomas J. Kowalski; Russell A. Garman

(57) ABSTRACT

Provided is a method of vaccinating a patient against a tumor by administering an agent to reduce or prevent interaction between Notch and a Notch ligand, or expression or processing of Notch or a Notch ligand. In one embodiment, this is accomplished by administering to the patient a tumor antigen expressed by the tumor and exposing an antigen presenting cell in the patient to an agent that reduces or prevents interaction, expression or processing of Notch or a Notch ligand in a T cell.

12 Claims, 2 Drawing Sheets

OTHER PUBLICATIONS

Figure 1:
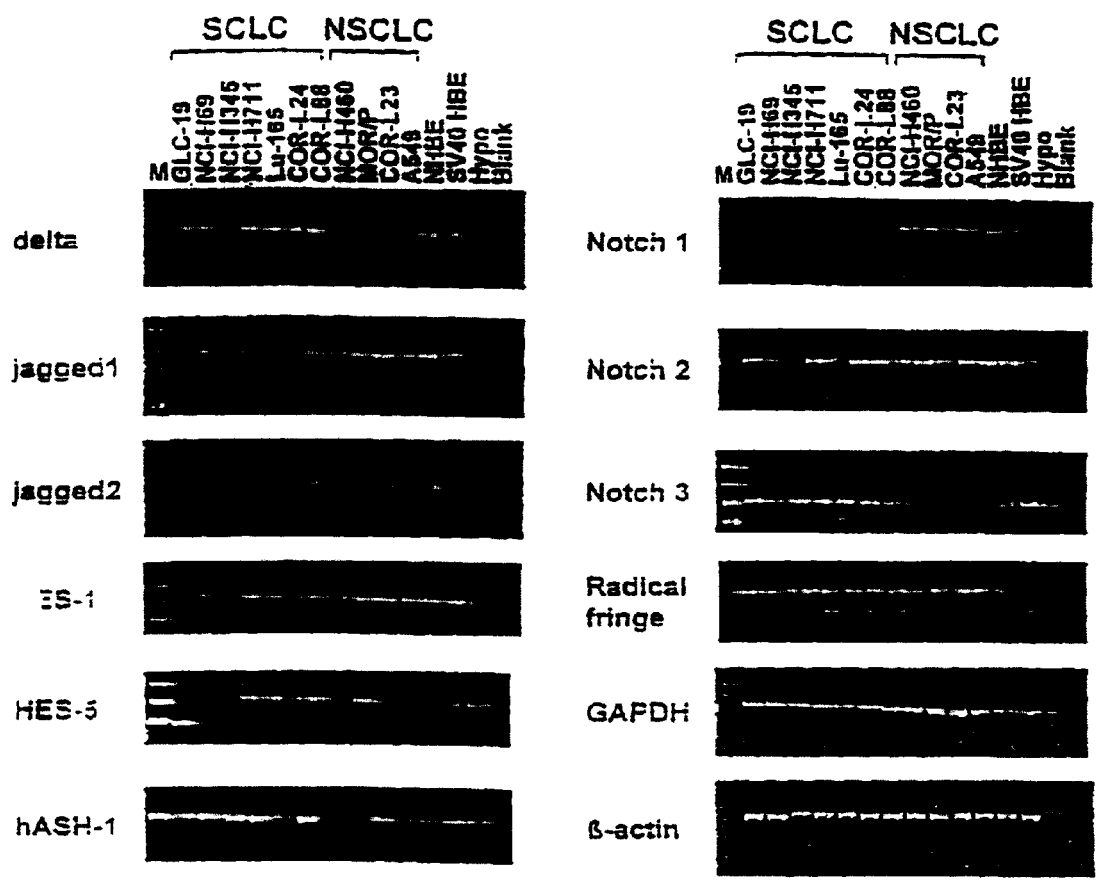

Inaba K, et al. (1992) J. Exp. Med. 175: 1157-1167.
Caux C, et al. (1992) Nature 360: 258-261.
Zhao et al. (1995) J. Immunol 155:3904-3911.
Wilson and Hemmati-Brivanlou (1997) Neuron 18: 699-710.
Hemmati-Brivanlou and Melton (1997) Cell.
Valenzuela et al. (1995) J. Neurosci 15: 6077-6084.
Sasai et al. (1994) Cell 79: 779-790.
Shimizu et al (1999) J. Biol. Chem. 274(46): 32961-32969.
Iemura etal. (1998) PNAS 95: 9337-9342.
Duojia Pan et al (1997) Cell 90: 271-280.
Altman et al. (1996) Science 274; 94-96.
Vose et al. (1977) Eur. J. Immunol. 7:753-757.
Belldegrun et al. (1988) Cancer Research 48: 206-214.
Belldegrun et al. (1988) The Journal of Immunology 142(12): 4520-4526.
Dunbar et al. (1998) Current Biology 8:413-416.
Lamb et al. (1983) J. Exp. Med 157: 1434-1447.
Eddison et al. (2000) PNAS 97(22) 11692-11699.
Sallusto F and Lanzavecchia A (1994) J. Exp. Med. 179: 1109-1118.
Lee et al. (2000) Current Biology 10:931-934.
Linheng et al. (1998) Immunity 8:43-55.
Medzhitov et al. (1997) Nature 388:384-397.
Romero et al. (1998) J. Exp. Med. 188(9) 1641-1650.
Spiess et al. (1987) JNC179(5) 1067-1075.
Takahashi et al. (2000) Nature Genetics 25: 390-396.

* cited by examiner

SEQUENCE LISTING

<160> NUMBER OF SEQ ID NOS: 24

<210> SEQ ID NO 1
<211> LENGTH: 23
<212> TYPE: DNA
<213> ORGANISM: Homo Sapiens

<400> SEQUENCE: 1
ttttctgcaa ccaggacctg aac                                                 23

<210> SEQ ID NO 2
<211> LENGTH: 23
<212> TYPE: DNA
<213> ORGANISM: Homo Sapiens

<400> SEQUENCE: 2
cacacacttg gcaccattag aac                                                 23

<210> SEQ ID NO 3
<211> LENGTH: 24
<212> TYPE: DNA
<213> ORGANISM: Homo Sapiens

<400> SEQUENCE: 3
tgacaaatat cagtgttcct gccc                                                24

<210> SEQ ID NO 4
<211> LENGTH: 24
<212> TYPE: DNA
<213> ORGANISM: Homo Sapiens

<400> SEQUENCE: 4
agcgataacc attaaccaaa tccc                                                24

<210> SEQ ID NO 5
<211> LENGTH: 20
<212> TYPE: DNA
<213> ORGANISM: Homo Sapiens

<400> SEQUENCE: 5
tgggactggg acaacgatac                                                     20

<210> SEQ ID NO 6
<211> LENGTH: 24
<212> TYPE: DNA
<213> ORGANISM: Homo Sapiens

<400> SEQUENCE: 6
gcaaattaca cccttgttta caca                                                24

<210> SEQ ID NO 7
<211> LENGTH: 20
<212> TYPE: DNA
<213> ORGANISM: Homo Sapiens

<400> SEQUENCE: 7
aatggagaat tcctcctccc                                                     20

<210> SEQ ID NO 8
<211> LENGTH: 20
<212> TYPE: DNA
<213> ORGANISM: Homo Sapiens

```
<400> SEQUENCE: 8
tcacctcgtt catgcactcg                                               20

<210> SEQ ID NO 9
<211> LENGTH: 18
<212> TYPE: DNA
<213> ORGANISM: Homo Sapiens

<400> SEQUENCE: 9
aaggagaaaa accgactg                                                 18

<210> SEQ ID NO 10
<211> LENGTH: 19
<212> TYPE: DNA
<213> ORGANISM: Homo Sapiens

<400> SEQUENCE: 10
tgtgtttcag gtagctgac                                                19

<210> SEQ ID NO 11
<211> LENGTH: 24
<212> TYPE: DNA
<213> ORGANISM: Homo Sapiens

<400> SEQUENCE: 11
aacaagaaga tgagtaaggt ggag                                          24

<210> SEQ ID NO 12
<211> LENGTH: 23
<212> TYPE: DNA
<213> ORGANISM: Homo Sapiens

<400> SEQUENCE: 12
tggagttcaa gtcgttggag tag                                           23

<210> SEQ ID NO 13
<211> LENGTH: 24
<212> TYPE: DNA
<213> ORGANISM: Homo Sapiens

<400> SEQUENCE: 13
gccagaactg tgaggaaaat atcg                                          24

<210> SEQ ID NO 14
<211> LENGTH: 20
<212> TYPE: DNA
<213> ORGANISM: Homo Sapiens

<400> SEQUENCE: 14
cagatggcct tgccattgac                                               20

<210> SEQ ID NO 15
<211> LENGTH: 23
<212> TYPE: DNA
<213> ORGANISM: Homo Sapiens

<400> SEQUENCE: 15
taactccttc tcttgcttgt gcc                                           23

<210> SEQ ID NO 16
<211> LENGTH: 23
<212> TYPE: DNA
```

<213> ORGANISM: Homo Sapiens

<400> SEQUENCE: 16
acacactcgc atctgtatcc acc                                    23

<210> SEQ ID NO 17
<211> LENGTH: 20
<212> TYPE: DNA
<213> ORGANISM: Homo Sapiens

<400> SEQUENCE: 17
taggagggag aagccaagtc                                        20

<210> SEQ ID NO 18
<211> LENGTH: 20
<212> TYPE: DNA
<213> ORGANISM: Homo Sapiens

<400> SEQUENCE: 18
aaaaaggcaa taggccccag                                        20

<210> SEQ ID NO 19
<211> LENGTH: 24
<212> TYPE: DNA
<213> ORGANISM: Homo Sapiens

<400> SEQUENCE: 19
atgacaatta tgtgaacgca agga                                   24

<210> SEQ ID NO 20
<211> LENGTH: 24
<212> TYPE: DNA
<213> ORGANISM: Mouse

<400> SEQUENCE: 20
accagtagca aaccagaact tgac                                   24

<210> SEQ ID NO 21
<211> LENGTH: 20
<212> TYPE: DNA
<213> ORGANISM: Mouse

<400> SEQUENCE: 21
ggctgggaag gaacaacctg                                        20

<210> SEQ ID NO 22
<211> LENGTH: 22
<212> TYPE: DNA
<213> ORGANISM: Mouse

<400> SEQUENCE: 22
ggtagccatt gatctcatcc ac                                     22

<210> SEQ ID NO 23
<211> LENGTH: 20
<212> TYPE: DNA
<213> ORGANISM: Mouse

<400> SEQUENCE: 23
gattctcctg atgacctcgc                                        20

<210> SEQ ID NO 24
<211> LENGTH: 20

```
<212> TYPE: DNA
<213> ORGANISM: Mouse

<400> SEQUENCE: 24
gtgttcgtca cacacgaagc                                                    20
```

US 7,678,758 B2

METHOD FOR ENHANCING T CELL REACTIVITY TOWARD TUMOUR ANTIGENS

CROSS REFERENCE TO RELATED APPLICATIONS

This application is a Continuation-in-Part of PCT/GB00/04391, filed Nov. 17, 2000, designating the U.S., published May 25, 2001 as WO 01/35990 and claiming priority from GB 9927328.6, filed Nov. 18, 1999. This application makes reference to U.S. Ser. No. 09/310,685, filed May 4, 1999. All of the above-mentioned applications, as well as all documents cited herein and documents referenced or cited in documents cited herein, are hereby incorporated by reference.

FIELD OF THE INVENTION

The present invention relates to methods for enhancing the response of T cells to tumour cells. These methods may be used in tumour immunotherapy.

BACKGROUND TO THE INVENTION

Although significant advances have been made in recent years in the development of treatments for cancer, many of the resulting treatments are still based on administration of toxic compounds with consequential side-effects. As an alternative form of therapy, attempts have been made to enhance the patient's own immune response against tumours with varying degrees of success. It is not really understood how tumour cells escape recognition by the host immune system and/or inhibit an immune response. For example, it has been known for several years that a variety of immune cell-types infiltrate solid tumours in large numbers yet fail to mount an effective immunological response to the tumour. Indeed, it is possible to isolate tumour infiltrating lymphocytes which contain T cells with T cell receptors specific for tumour antigens in vitro which fail to be activated by tumour tissue in vivo. Thus there is need in the art for therapeutic methods that are capable of overcoming this immunosuppressive effect exerted by tumour cell in vivo.

Ligands that bind to cell surface receptors of the Notch family have recently been shown to be expressed on the surface of cells of the immune system, such as antigen presenting cells (APCs) and T-lymphocytes and a role for these molecules in such cells has been demonstrated in the regulation of tolerance induction (WO-A-98/20142).

It has recently been shown that it is possible to generate a class of regulatory T cells which are able to transmit antigen-specific tolerance to other T cells, a process termed infectious tolerance (WO-A-98/20142). The functional activity of these cells can be mimicked by over-expression of a Notch ligand protein on their cell surfaces. In particular, regulatory T cells can be generated by over-expression of a member of the Delta or Serrate family of Notch ligand proteins. Delta or Serrate expressing T cells specific to one antigenic epitope are also able to transfer tolerance to T cells recognising other epitopes on the same or related antigens, a phenomenon termed "epitope spreading".

SUMMARY OF THE PRESENT INVENTION

We have now found that the expression of Notch ligands is upregulated in some tumour cells. We have also shown that tumour cells that express a Notch ligand are capable of rendering T cells unresponsive to restimulation with specific antigen. Consequently, this may provide one possible means by which tumour cells may inhibit T cell responses. This conclusion is supported further by our previous results showing that upregulation of Notch ligand expression can induce immunotolerance (WO-A-98/20142). Thus, by preventing this mechanism operating in T cells in vivo, it may be possible to prevent tumour cells inducing immunotolerance in T cells that recognise tumour-specific antigens in the tumour cells. This would then allow the T cells to mount an immune response against the tumour cells.

Accordingly the present invention provides a method for enhancing the reactivity of a T cell toward a tumour cell which method comprises:
(a) isolating a T cell which preferably is a tumour infiltrating lymphocyte from a patient having said tumour cell present in their body;
(b) exposing the cell to an agent, which agent is capable of reducing or preventing expression of Notch or a Notch ligand in the cell; and
(c) re-introducing the cell into the patient;
wherein the T cell comprises a T cell receptor specific for a tumour antigen expressed by the tumour cell.

The present invention further provides a method for enhancing the reactivity of a T cell toward a tumour cell which method comprises:
(a) isolating an antigen presenting cell (APC) from a tumour present in the body of a patient;
(b) exposing the APC to an agent, which agent is capable of reducing or preventing expression of a Notch ligand in the T cell when the T cell is contacted with the transfected APC; and
(c) re-introducing the APC into the patient.

According to a further aspect, the present invention provides a method for enhancing the reactivity of a T cell toward a tumour cell which method comprises:
(a) isolating a tumour cell from a tumour present in the body of a patient;
(b) exposing the tumour cell to an agent, which is capable of reducing or preventing expression or interaction of an endogenous Notch or Notch ligand in the T cell when the T cell is contacted with the tumour cell; and
(c) re-introducing the tumour cell into the patient.

In one preferred embodiment step (b) comprises introducing a nucleic acid sequence into the cell, APC or tumour cell, which sequence is capable of reducing or preventing expression of Notch or a Notch ligand in the cell, APC or tumour cell.

Preferably the nucleic acid sequence encodes a polypeptide selected from Toll-like receptor protein family (Medzhitov et al., 1997), a cytokine such as IL-12, IFN-γ, TNF-α, or a growth factor such as a bone morphogenetic protein (BMP), a BMP receptor and activins. Preferably the polypeptide that decreases or interferes with the production of agents that are capable of producing an increase in the expression of Notch ligand, such as Noggin, Chordin, Follistatin, Xnr3; fibroblast growth factors and derivatives, fragments, variants and homologues thereof.

Alternatively, the nucleic acid sequence is an antisense construct derived from a sense nucleotide sequence encoding a polypeptide selected from a Notch ligand and a polypeptide capable of upregulating Notch ligand expression, such as Noggin, Chordin, Follistatin, Xnr3, fibroblast growth factors and derivatives, fragments, variants and homologues thereof.

In another preferred embodiment the agent is a chemical compound such as a polypeptide which is exposed/incubated with the cell, APC or tumour cell. The agent should be one which is capable of modulating Notch-Notch ligand interactions. In this embodiment the polypeptide is preferably selected from a Toll-like receptor, a cytokine such as IL-12, IFN-γ, TNF-α, or a growth factor such as a BMP, a BMP receptor and activins. Preferably the polypeptide decreases or interferes with the production of an agent that is capable of producing an increase in the expression of Notch ligand, such as Noggin, Chordin, Follistatin, Xnr3, fibroblast growth factors and derivatives, fragments, variants, homologues and analogs thereof.

Preferably when the agent is a receptor or a nucleic acid sequence encoding a receptor, the receptor is activated. Thus, e.g., when the agent is a nucleic acid sequence, the receptor is constitutively active when expressed.

As used herein, the terms protein and polypeptide may be assumed to be synonymous, protein merely being used in a general sense to indicate a relatively longer amino acid sequence than that present in a polypeptide.

The term "derivative" as used herein, in relation to proteins or polypeptides of the present invention includes any substitution of, variation of, modification of, replacement of, deletion of or addition of one (or more) amino acid residues from or to the sequence providing that the resultant protein or polypeptide possesses the capability of modulating Notch-Notch ligand interactions.

The term "variant" as used herein, in relation to proteins or polypeptides of the present invention includes any substitution of, variation of, modification of, replacement of, deletion of or addition of one (or more) amino acid residues from or to the sequence providing that the resultant protein or polypeptide possesses the capability of modulating Notch-Notch ligand interactions.

The term "analog" are used herein, in relation to the proteins or polypeptides of the present invention includes any peptidomimetic, that is, a chemical compound that possesses the capability of modulating Notch-Notch ligand interactions in a similar manner to the parent protein or polypeptide. These include compounds that may antagonise the expression or activity of a Notch-protein or Notch-ligand.

An agent may be considered to modulate Notch-Notch ligand interactions if it is capable of inhibiting the interaction of Notch with its ligands, preferably to an extent sufficient to provide therapeutic efficacy.

In a preferred embodiment the agent modulates Notch-Notch ligand interactions by being capable of reducing or preventing expression of Notch or Notch ligand.

The expression "Notch-Notch ligand" as used herein means the interaction between a Notch family member and a ligand capable of binding to one or more such member. Thus by the expression "reducing or preventing interaction of Notch or a Notch-ligand" we mean inhibiting the interaction of Notch in a T cell, APC or tumour cell with a Notch ligand or inhibiting the interaction of a Notch ligand in a T cell, APC or tumour cell with Notch.

The term therapy are used herein should be taken to encompass diagnostic and prophylatic applications.

Preferably the endogenous Notch ligand is selected from Serrate, Delta and homologues thereof, more preferably Serrate and Delta.

The present invention also provides a method of vaccinating a patient against a tumour which method comprises:
(a) administering a tumour antigen expressed by the tumour to the skin of the patient; and
(b) exposing an agent to an APC present in the skin of the patient wherein the agent is capable of inhibiting or preventing expression of a Notch ligand in a T cell.

In particular, where the nucleic acid sequence is introduced into an APC, the sequence is preferably capable of inhibiting or reducing the expression of Serrate-1 since expression of Serrate-1 is down-regulated in APCs during an effective immune response and up-regulated in conditions of immune tolerance i.e. Serrate-1 is a mediator of tolerance induction. An example of a suitable sequence is therefore a sequence an activated Toll-like receptor (for example TLR-2, TLR-4) which would lead to decreased expression of Serrate-1, Serrate-2, Delta-1 and Delta-3.

DETAILED DESCRIPTION OF THE INVENTION

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA* Methods in Enzymology, Academic Press; and E. M. Shevach and W. Strober, 1992 and periodic suppliements, *Current Protocols in Immunology*, John Wiley & Sons, New York, N.Y. Each of these general texts is herein incorporated by reference.

Notch and Notch Ligands

An endogenous Notch or Notch ligand in the context of the present invention is a polypeptide encoded by the genome of a mammalian cell that is capable of being expressed by the mammalian cell. In particular the mammalian cell may be a hemapoietic cell such as a T-cell or an antigen presenting cell. The endogenous Notch ligand is typically is capable of binding to a Notch receptor polypeptide present in the membrane of a variety of mammalian cell types, for example hemapoietic stem cells. At least four Notch receptors (Notch-1, Notch-2, Notch-3 and Notch-4) have been identified to date in human cells.

Particular examples of mammalian Notch ligands identified to date include the Delta family, for example Delta (Genbank Accession No. AF003522—*Homo sapiens*), Delta-3 (Genbank Accession No. AF084576—*Rattus norvegicus*) and Delta-like 3 (*Mus musculus*), the Serrate family, for example Serrate-1 and Serrate-2 (WO97/01571, WO96/27610 and WO92/19734), Jagged-1 and Jagged-2 (Genbank Accession No. AF029778—*Homo sapiens*), and LAG-2. Homology between family members is extensive. For example, human Jagged-2 has 40.6% identity and 58.7% similarity to Serrate.

Further homologues of known mammalian Notch ligands may be identified using standard techniques. By a "homologue" it is meant a gene product that exhibits sequence homology, either amino acid or nucleic acid sequence homology, to any one of the known Notch ligands, for example as mentioned above. Typically, a homologue of a known Notch ligand will be at least 20%, preferably at least 30%, identical at the amino acid level to the corresponding known Notch ligand. Techniques and software for calculating sequence homology between two or more amino acid or nucleic acid sequences are well known in the art (see for example Ausubel et al., Current Protocols in Molecular Biology (1995), John Wiley & Sons, Inc. and databases created by the National Center for Biotechnology Information.)

Notch ligands identified to date have a diagnostic DSL domain (D. Delta, S. Serrate, L. Lag2) comprising 20 to 22 amino acids at the amino terminus of the protein and between 3 to 8 EGF-like repeats on the extracellular surface. It is therefore preferred that homologues of Notch ligands also comprise a DSL domain at the N-terminus and between 3 to 8 EGF-like repeats on the extracellular surface.

In addition, suitable homologues will be capable of binding to a Notch receptor. Binding may be assessed by a variety of techniques known in the art including in vitro binding assays.

Homologues of Notch ligands can be identified in a number of ways, for example by probing genomic or cDNA libraries with probes comprising all or part of a nucleic acid encoding a Notch ligand under conditions of medium to high stringency (for example 0.03M sodium chloride and 0.03M sodium citrate at from about 50° C. to about 60° C.). Alternatively, homologues may also be obtained using degenerate PCR which will generally use primers designed to target sequences within the variants and homologues encoding conserved amino acid sequences. The primers will contain one or more degenerate positions and will be used at stringency conditions lower than those used for cloning sequences with single sequence primers against known sequences.

Nucleic Acid Sequences Capable of Reducing or Preventing Endogenous Notch Ligand Expression Substances that may be used to inhibit Notch ligand expression include nucleic acid sequences encoding polypeptides that affect the expression of genes encoding Notch ligands. For instance, for Delta expression, binding of extracellular BMPs (bone morphogenetic proteins, Wilson and Hemmati-Brivanlou, 1997; Hemmati-Brivanlou and Melton, 1997) to their receptors leads to down-regulated Delta transcription due to the inhibition of the expression of transcription factors of the achaete/scute complex. This complex is believed to be directly involved in the regulation of Delta expression. Thus, any polypeptide that upregulates BMP expression and/or stimulates the binding of BMPs to their receptors may be capable of producing a decrease in the expression of Notch ligands such as Delta and/or Serrate. Examples may include nucleic acids encoding BMPs themselves. Furthermore, any substance that inhibits expression of transcription factors of the achaete/scute complex may also downregulate Notch ligand expression.

Members of the BMP family include BMP1 to BMP6, BMP7 also called OP1, OP2 (BMP8) and others. BMPs belong to the transforming growth factor beta (TGF-beta) superfamily, which includes, in addition to the TGF-betas, activins/inhibins (e.g., alpha-inhibin), mullerian inhibiting substance, and glial cell line-derived neurotrophic factor.

Other examples of polypeptides that inhibit the expression of Delta and/or Serrate include the Toll-like receptor (Medzhitov et al., 1997) or any other receptors linked to the innate immune system (for example CD14, complement receptors, scavenger receptors or defensin proteins), and other polypeptides that decrease or interfere with the production of Noggin (Valenzuela et al., 1995), Chordin (Sasai et al., 1994), Follistatin (Iemura et al., 1998), Xnr3, and derivatives and variants thereof. Noggin and Chordin bind to BMPs thereby preventing activation of their signalling cascade which leads to decreased Delta transcription. Consequently, reducing Noggin and Chordin levels may lead to decrease Notch ligand, in particular Delta, expression.

In more detail, in Drosophila, the Toll transmembrane receptor plays a central role in the signalling pathways that control amongst other things the innate nonspecific immune response. This Toll-mediated immune response reflects an ancestral conserved signalling system that has homologous components in a wide range of organisms. Human Toll homologues have been identified amongst the Toll-like receptor (TLR) genes and Toll/interleukin-1 receptor-like (TIL) genes and contain the characteristic Toll motifs: an extracellular leucine-rich repeat domain and a cytoplasmic interleukin-1 receptor-like region. The Toll-like receptor genes (including TIL genes) now include TLR4, TIL3, TIL4, and 4 other identified TLR genes.

Other suitable sequences that may be used to downregulate Notch ligand expression include Mesp2 (Takahashi et al., 2000), those encoding immune costimulatory molecules (for example CD80, CD86, ICOS, SLAM) and other accessory molecules that are associated with immune potentiation (for example CD2, LFA-1).

Other suitable substances that may be used to downregulate Notch ligand expression include nucleic acids that inhibit the effect of transforming growth factors such as members of the fibroblast growth factor (FGF) family. The FGF may be a mammalian basic FGF, acidic FGF or another member of the FGF family such as an FGF-1, FGF-2, FGF-3, FGF-4, FGF-5, FGF-6, FGF-7. Preferably the FGF is not acidic FGF (FGF-1; Zhao et al., 1995). Most preferably, the FGF is a member of the FGF family which acts by stimulating the upregulation of expression of a Serrate polypeptide on APCs. The inventors have shown that members of the FGF family can upregulate Serrate-1 gene expression in APCs.

Suitable nucleic acid sequences may include anti-sense constructs, for example nucleic acid sequences encoding anti-sense Notch ligand constructs as well as antisense constructs designed to reduce or inhibit the expression of upregulators of Notch ligand expression (see above). The antisense nucleic acid may be an oligonucleotide such as a synthetic single-stranded DNA. However, more preferably, the antisense is an antisense RNA produced in the patient's own cells as a result of introduction of a genetic vector. The vector is responsible for production of antisense RNA of the desired specificity on introduction of the vector into a host cell.

Preferably, the nucleic acid sequence for use in the present invention is capable of inhibiting Serrate and Delta, preferably Serrate 1 and Serrate 2 as well as Delta 1 and Delta 3 expression in APCs such as dendritic cells. In particular, the nucleic acid sequence may be capable of inhibiting Serrate expression but not Delta expression in APCs. Alternatively, the nucleic acid sequence for use in the present invention is capable of inhibiting Delta expression in T cells such as CD4$^+$ helper T cells or other cells of the immune system that express Delta (for example in response to stimulation of cell surface receptors). In particular, the nucleic acid sequence may be capable of inhibiting Delta expression but not Serrate expression in T cells. In a particularly preferred embodiment, the nucleic acid sequence is capable of inhibiting Notch ligand expression in both T cells and APC, for example Serrate expression in APCs and Delta expression in T cells.

Suitable nucleic acid sequences for use according to the present invention may be conveniently identified using a simple screening procedure. In one such assay procedure, T cells, APCs or tumour cells in culture may be transfected with a candidate sequence and the effect on expression of an endogenous Notch ligand, such as Delta or Serrate, determined in the presence or absence of a suitable stimulus (such as an antigen) for example by (i) measuring transcription initiated from the gene encoding the Notch ligand (see, for example WO-A-98/20142) or by quantitative-reverse transcriptase-polymerase chain reaction (RT-PCR)(see Example 1); (ii) detecting Notch ligand protein by techniques such as Western blotting of cell extracts, immunohistochemistry or flow cytometry; and/or (iii) functional assays such as cell adhesion assays.

Compounds Capable of Reducing or Preventing Notch or Notch Ligand Expression or Interaction Substances that may be used to inhibit Notch and Notch ligand expression polypeptides and conventional chemical compounds. The polypeptides may be the expression products of the nucleic acid sequences mentioned above in section B.

Preferred suitable substances that may be used to downregulate Notch ligand expression include growth factors and cytokines. More preferably soluble protein growth factors may be used to inhibit Notch or Notch ligand expression on APCs, T cells or tumour cells in culture by the addition of exogenous growth factors. For instance, Notch ligand expression may be reduced or inhibited by the addition of BMPs or activins (a member of the TGF-b superfamily). In addition, T cells, APCs or tumour cells could be cultured in the presence of inflammatory type cytokines including IL-12, IFN-γ, IL-18, TNF-α, either alone or in combination with BMPs.

The present invention also relates to modification of Notch-protein expression or presentation on the cell membrane or signalling pathways. Agents that reduce or interfere with its presentation as a fully functional cell membrane protein may include MMP inhibitors such as hydroxymate-based inhibitors.

Other substances which may be used to reduce interaction between Notch and Notch ligands are exogenous Notch or Notch ligands or functional derivatives thereof. Such Notch ligand derivatives would preferably have the DSL domain at the N-terminus and between 3 to 8 EGF-like repeats on the extracellular surface. A peptide corresponding to the Delta/Serrate/LAG-2 domain of hJagged1 and supernatants from COS cells expressing a soluble form of the extracellular portion of hJagged1 was found to mimic the effect of Jagged1 in inhibiting Notch1 (Li et al., 1998). Other substances which may be used to reduce interaction between Notch and Notch ligands include, for example, Numb (Eddison et al., 2000) and Scabrous (Lee et al., 2000).

Whether a substance can be used for modulating Notch-Notch ligand expression may be determined using suitable screening assays.

Screening assays for the detection of decreased Notch, Notch ligand expression and/or processing include:

Notch-Notch ligand expression may be assessed following exposure of isolated cells to test compounds in culture using for example:

(a) at the protein level by specific antibody staining using immunohistochemistry or flow cytometry.

(b) at the RNA level by quantitative—reverse transcriptase-polymerase chain reaction (RT-PCR). RT-PCR may be performed using a control plasmid with in-built standards for measuring endogenous gene expression with primers specific for Notch 1 and Notch 2, Serrate 1 and Serrate 2, Delta 1 and Delta 2 and Delta 3. This construct may be modified as new ligand members are identified.

(c) at the functional level in cell adhesion assays.

Decreased Notch ligand or Notch expression should lead to decreased adhesion between cells expressing Notch and its ligands. Test cells will be exposed to a particular treatment in culture and radiolabelled or flourescein labelled target cells (transfected with Notch/Notch ligand protein) will be overlayed. Cell mixtures will be incubated at 37° C. for 2 hours. Nonadherent cells will be washed away and the level of adherence measured by the level of radioactivity/immunofluorescence at the plate surface.

Using such methods it is possible to detect compounds or Notch-ligands that affect the expression or processing of a Notch-protein or Notch-ligand. The invention also relates to compounds, or Notch-ligands detectable by these assays methods, and also to their use in the methods of the present invention.

Antibodies

In one embodiment the agent for reducing or preventing interaction, expression or processing of Notch or a Notch ligand may be an antibody.

The term "antibody" as used herein includes intact molecules as well as fragments thereof, such as Fab, Fab', F(ab')$_2$, Fv and scFv which are capable of binding the epitopic determinant. These antibody fragments retain some ability to selectively bind with its antigen or receptor and include, for example:

(i) Fab, the fragment which contains a monovalent antigen-binding fragment of an antibody molecule can be produced by digestion of whole antibody with the enzyme papain to yield an intact light chain and a portion of one heavy chain;

(ii) Fab', the fragment of an antibody molecule can be obtained by treating whole antibody with pepsin, followed by reduction, to yield an intact light chain and a portion of the heavy chain; two Fab' fragments are obtained per antibody molecule;

(iii) F(ab')$_2$, the fragment of the antibody that can be obtained by treating whole antibody with pepsin without subsequent reduction; F(ab')$_2$ is a dimer of two Fab' fragments held together by two disulfide bonds;

(iv) Fv, defined as a genetically engineered fragment containing the variable genetically fused single chain molecule.

General methods of making these fragments are known in the art. (See for example, Harlow and Lane, Antibodies: A Laboratory Manual, Cold Spring Harbor Laboratory, New York (1988), the text of which is incorporated herein by reference). Antibodies may be monoclonal or polyclonal but are preferably monoclonal.

Suitably, the binding affinity (equilibrium association constant (Ka)) may be at least about $10^6$ M$^{-1}$, at least about $10^7$ M$^{-1}$, at least about $10^8$ M$^{-1}$ or at least about $10^9$ M$^{-1}$.

Suitably the agents block binding of human Notch to human Delta and/or Serrate by at least about 10%, 20%, 30%, 40%, 50%, 60%, 70%, 80%, 90%, 99%, or 100%.

Suitable antibodies for use as modulating agents are obtained by immunizing a host animal with peptides comprising all or a portion of Notch or a Notch ligand such as Delta or Serrate/Jagged.

The peptide used may comprise the complete protein or a fragment or derivatives thereof. Preferred immunogens comprise all or a part of the extracellular domain of human Notch, Delta or Serrate/Jagged, where these residues contain any post-translation modifications, such as glycosylation, found in the native proteins. Immunogens comprising the extracellular domain may be produced by a number of techniques which are well known in the art such as expression of cloned genes using conventional recombinant methods and/or isolation from T cells or cell populations expressing high levels of Notch or Notch ligands.

Monoclonal antibodies may be produced by means well known in the art. Generally, the spleen and/or lymph nodes of an immunized host animal provide a source of plasma cells.

The plasma cells are immortalized by fusion with myeloma cells to produce hybridoma cells. Culture supernatant from individual hybridomas is screened using standard techniques to identify those producing antibodies with the desired specificity. The antibody may be purified from the hybridoma cell supernatants or ascites fluid by conventional techniques, such as affinity chromatography using Notch, Notch ligands or fragments thereof bound to an insoluble support, protein A sepharose, or the like.

The choice of isotype will be guided by the desired effector functions, such as complement fixation, or activity in antibody-dependent cellular cytotoxicity. Suitable isotypes include IgG 1, IgG3 and IgG4. Suitably, either of the human light chain constant regions, kappa or lambda, may be used.

For example, antibodies against Notch and Notch ligands are described in U.S. Pat. Nos. 5,648,464, 5,849,869 and 6,004,924 (Yale University/Imperial Cancer Technology), the texts of which are herein incorporated by reference.

Antibodies generated against the Notch receptor are also described in WO 0020576 (the text of which is also incorporated herein by reference). For example, this document discloses generation of antibodies against the human Notch-1 EGF-like repeats 11 and 12. For example, in particular embodiments, WO 0020576 discloses a monoclonal antibody secreted by a hybridoma designated A6 having the ATCC Accession No. HB12654, a monoclonal antibody secreted by a hybridoma designated C11 having the ATCC Accession No. HB12656 and a monoclonal antibody secreted by a hybridoma designated F3 having the ATCC Accession No. HB12655.

Preferably, antibodies for use to treat human patients will be chimeric or humanised antibodies. Antibody "humanisation" techniques are well known in the art. These techniques typically involve the use of recombinant DNA technology to manipulate DNA sequences encoding the polypeptide chains of the antibody molecule.

As described in U.S. Pat. No. 5,859,205 early methods for humanising monoclonal antibodies (Mabs) involved production of chimeric antibodies in which an antigen binding site comprising the complete variable domains of one antibody is linked to constant domains derived from another antibody. Such chimerisation procedures are described in EP-A-0120694 (Celltech Limited), EP-A-0125023 (Genentech Inc. and City of Hope), EP-A-0 171496 (Res. Dev. Corp. Japan), EP-A-0 173 494 (Stanford University), and WO 86/01533 (Celltech Limited). For example, WO 86/01533 discloses a process for preparing an antibody molecule having the variable domains from a mouse MAb and the constant domains from a human immunoglobulin.

In an alternative approach, described in EP-A-0239400 (Winter), the complementarity determining regions (CDRs) of a mouse MAb are grafted onto the framework regions of the variable domains of a human immunoglobulin by site directed mutagenesis using long oligonucleotides. Such CDR-grafted humanised antibodies are much less likely to give rise to an anti-antibody response than humanised chimeric antibodies in view of the much lower proportion of non-human amino acid sequence which they contain. Examples in which a mouse MAb recognising lysozyme and a rat MAb recognising an antigen on human T-cells were humanised by CDR-grafting have been described by Verhoeyen et al (Science, 239, 1534-1536, 1988) and Riechmann et al (Nature, 332, 323-324, 1988) respectively. The preparation of CDR-grafted antibody to the antigen on human T cells is also described in WO 89/07452 (Medical Research Council).

In WO 90/07861 Queen et al propose four criteria for designing humanised immunoglobulins. The first criterion is to use as the human acceptor the framework from a particular human immunoglobulin that is unusually homologous to the non-human donor immunoglobulin to be humanised, or to use a consensus framework from many human antibodies. The second criterion is to use the donor amino acid rather than the acceptor if the human acceptor residue is unusual and the donor residue is typical for human sequences at a specific residue of the framework. The third criterion is to use the donor framework amino acid residue rather than the acceptor at positions immediately adjacent to the CDRs. The fourth criterion is to use the donor amino acid residue at framework positions at which the amino acid is predicted to have a side chain atom within about 3 A of the CDRs in a three-dimensional immunoglobulin model and to be capable of interacting with the antigen or with the CDRs of the humanised immunoglobulin. It is proposed that criteria two, three or four may be applied in addition or alternatively to criterion one, and may be applied singly or in any combination.

Polypeptides and Polynucleotides

Amino Acid Sequences

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "protein".

"Peptide" usually refers to a short amino acid sequence that is 10 to 40 amino acids long, preferably 10 to 35 amino acids.

The amino acid sequence may be prepared and isolated from a suitable source, or it may be made synthetically or it may be prepared by use of recombinant DNA techniques.

Nucleotide Sequences

As used herein, the term "nucleotide sequence" is synonymous with the term "polynucleotide".

The nucleotide sequence may be DNA or RNA of genomic or synthetic or of recombinant origin. They may also be cloned by standard techniques. The nucleotide sequence may be double-stranded or single-stranded whether representing the sense or antisense strand or combinations thereof.

Longer nucleotide sequences will generally be produced using recombinant means, for example using a PCR (polymerase chain reaction) cloning techniques. This will involve making a pair of primers (e.g. of about 15 to 30 nucleotides) flanking a region of the targeting sequence which it is desired to clone, bringing the primers into contact with mRNA or cDNA obtained from an animal or human cell, performing a polymerase chain reaction (PCR) under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector. In general, primers will be produced by synthetic means, involving a step wise manufacture of the desired nucleic acid sequence one nucleotide at a time. Techniques for accomplishing this using automated techniques are readily available in the art.

"Polynucleotide" refers to a polymeric form of nucleotides of at least 10 bases in length and up to 1,000 bases or even more, either ribonucleotides or deoxyribonucleotides or a modified form of either type of nucleotide. The term includes single and double stranded forms of DNA.

These may be constructed using standard recombinant DNA methodologies. The nucleic acid may be RNA or DNA and is preferably DNA. Where it is RNA, manipulations may be performed via cDNA intermediates. Generally, a nucleic acid sequence encoding the first region will be prepared and suitable restriction sites provided at the 5' and/or 3' ends. Conveniently the sequence is manipulated in a standard laboratory vector, such as a plasmid vector based on pBR322 or pUC19 (see below). Reference may be made to Molecular Cloning by Sambrook et al. (Cold Spring Harbor, 1989) or similar standard reference books for exact details of the appropriate techniques.

Sources of nucleic acid may be ascertained by reference to published literature or databanks such as GenBank. Nucleic acid encoding the desired first or second sequences may be obtained from academic or commercial sources where such sources are willing to provide the material or by synthesising or cloning the appropriate sequence where only the sequence data are available. Generally this may be done by reference to literature sources which describe the cloning of the gene in question.

Alternatively, where limited sequence data is available or where it is desired to express a nucleic acid homologous or otherwise related to a known nucleic acid, exemplary nucleic acids can be characterised as those nucleotide sequences which hybridise to the nucleic acid sequences known in the art.

For some applications, preferably, the nucleotide sequence is DNA. For some applications, preferably, the nucleotide sequence is prepared by use of recombinant DNA techniques (e.g. recombinant DNA). For some applications, preferably, the nucleotide sequence is cDNA. For some applications, preferably, the nucleotide sequence may be the same as the naturally occurring form.

The nucleotide sequence may comprise, for example, a protein-encoding domain, an antisense sequence or a functional motif such as a protein-binding domain and includes variants, derivatives, analogues and fragments thereof. The term also refers to polypeptides encoded by the nucleotide sequence.

Variants, Derivatives, Analogues, Homologues and Fragments

In addition to the specific amino acid sequences and nucleotide sequences mentioned herein, the present invention also encompasses the use of variants, derivatives, analogues, homologues and fragments thereof.

In the context of the present invention, a variant of any given sequence is a sequence in which the specific sequence of residues (whether amino acid or nucleic acid residues) has been modified in such a manner that the polypeptide or polynucleotide in question retains at least one of its endogenous functions. A variant sequence can be modified by addition, deletion, substitution modification replacement and/or variation of at least one residue present in the naturally-occurring protein.

The term "derivative" as used herein, in relation to proteins or polypeptides of the present invention includes any substitution of, variation of, modification of, replacement of, deletion of and/or addition of one (or more) amino acid residues from or to the sequence providing that the resultant protein or polypeptide retains at least one of its endogenous functions.

The term "analogue" as used herein, in relation to polypeptides or polynucleotides includes any mimetic, that is, a chemical compound that possesses at least one of the endogenous functions of the polypeptides or polynucleotides which it mimics.

Typically, amino acid substitutions may be made, for example from 1, 2 or 3 to 10 or 20 substitutions provided that the modified sequence retains the required activity or ability. Amino acid substitutions may include the use of non-naturally occurring analogues.

Proteins of use in the present invention may also have deletions, insertions or substitutions of amino acid residues which produce a silent change and result in a functionally equivalent protein. Deliberate amino acid substitutions may be made on the basis of similarity in polarity, charge, solubility, hydrophobicity, hydrophilicity, and/or the amphipathic nature of the residues as long as the transport or modulation function is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | GAP |
| | | ILV |
| | Polar - uncharged | CSTM |
| | | NQ |
| | Polar - charged | DE |
| | | KR |
| AROMATIC | | HFWY |

As used herein, the term "protein" includes single-chain polypeptide molecules as well as multiple-polypeptide complexes where individual constituent polypeptides are linked by covalent or non-covalent means. As used herein, the terms "polypeptide" and "peptide" refer to a polymer in which the monomers are amino acids and are joined together through peptide or disulfide bonds. The terms subunit and domain may also refer to polypeptides and peptides having biological function.

"Fragments" are also variants and the term typically refers to a selected region of the polypeptide or polynucleotide that is of interest either functionally or, for example, in an assay. "Fragment" thus refers to an amino acid or nucleic acid sequence that is a portion of a full-length polypeptide or polynucleodtide.

Such variants may be prepared using standard recombinant DNA techniques such as site-directed mutagenesis. Where insertions are to be made, synthetic DNA encoding the insertion together with 5' and 3' flanking regions corresponding to the naturally-occurring sequence either side of the insertion site. The flanking regions will contain convenient restriction sites corresponding to sites in the naturally-occurring sequence so that the sequence may be cut with the appropriate enzyme(s) and the synthetic DNA ligated into the cut. The DNA is then expressed in accordance with the invention to make the encoded protein. These methods are only illustrative of the numerous standard techniques known in the art for manipulation of DNA sequences and other known techniques may also be used.

Polynucleotide variants will preferably comprise codon optimised sequences. Codon optimisation is known in the art as a method of enhancing RNA stability and therefor gene expression. The redundancy of the genetic code means that several different codons may encode the same amino-acid. For example, Leucine, Arginine and Serine are each encoded by six different codons. Different organisms show preferences in their use of the different codons. Viruses such as HIV, for instance, use a large number of rare codons. By changing a nucleotide sequence such that rare codons are replaced by the corresponding commonly used mammalian codons, increased expression of the sequences in mammalian target cells can be achieved. Codon usage tables are known in the art for mammalian cells, as well as for a variety of other organisms. Preferably, at least part of the sequence is codon optimised. Even more preferably, the sequence is codon optimised in its entirety.

As used herein, the term "homology" can be equated with "identity". An homologous sequence will be taken to include an amino acid sequence which may be at least 75, 85 or 90% identical, preferably at least 95 or 98% identical. In particular, homology should typically be considered with respect to those regions of the sequence (such as amino acids at positions 51, 56 and 57) known to be essential for an activity. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

Percent homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum % homology therefor firstly requires the production of an optimal alignment, taking into consideration gap penalties. A suitable computer program for carrying out such an alignment is the GCG Wisconsin Bestfit package (University of Wisconsin, U.S.A.; Devereux). Examples of other software than can perform sequence comparisons include, but are not limited to, the BLAST package, FASTA (Atschul) and the GENEWORKS suite of comparison tools. Both BLAST and FASTA are available for offline and online searching (see Ausubel et al., 1999 ibid, pages 7-58 to 7-60). However it is preferred to use the GCG Bestfit program.

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

Nucleotide sequences which are homologous to or variants of sequences of use in the present invention can be obtained in a number of ways, for example by probing DNA libraries made from a range of sources. In addition, other viral/bacterial, or cellular homologues particularly cellular homologues found in mammalian cells (e.g. rat, mouse, bovine and primate cells), may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of the reference nucleotide sequence under conditions of medium to high stringency. Similar considerations apply to obtaining species homologues and allelic variants of the amino acid and/or nucleotide sequences useful in the present invention.

Variants and strain/species homologues may also be obtained using degenerate PCR which will use primers designed to target sequences within the variants and homologues encoding conserved amino acid sequences within the sequences of use in the present invention. Conserved sequences can be predicted, for example, by aligning the amino acid sequences from several variants/homologues. Sequence alignments can be performed using computer software known in the art. For example the GCG Wisconsin PileUp program is widely used. The primers used in degenerate PCR will contain one or more degenerate positions and will be used at stringency conditions lower than those used for cloning sequences with single sequence primers against known sequences.

Alternatively, such nucleotide sequences may be obtained by site directed mutagenesis of characterised sequences. This may be useful where for example silent codon changes are required to sequences to optimise codon preferences for a particular host cell in which the nucleotide sequences are being expressed. Other sequence changes may be desired in order to introduce restriction enzyme recognition sites, or to alter the activity of the polynucleotide or encoded polypeptide.

Transgenic Animals

The present invention also relates to cell lines or transgenic animals which are capable of expressing or overexpressing Notch, a Notch ligand or at least one agent useful in the present invention. Preferably the cell line or animal expresses or overexpresses Notch, Delta or Serrate.

The present invention additionally relates to cell lines or transgenic animals which are capable of expressing or overexpressing at least one polypeptide which is capable of inhibiting Notch-Notch ligand interactions. Such agents have been described above and for the avoidance of doubt are specifically incorporated herein by reference.

The present invention further relates to cell lines or transgenic animals which are capable of expressing or overexpressing at least one polypeptide which is capable of enhancing Notch-Notch ligand interactions. Agents that enhance the presentation of a fully functional Notch-protein on the T cell or APC surface include matrix metalloproteinases such as the product of the Kuzbanian gene of Drosophila (Dkuz et al., (1997) and other ADAMALYSIN gene family members. Suitable agents that influence expression of Notch-ligands include agents that affect the expression of Delta and/or Serrate genes. For instance, for Delta expression, any agent that inhibits the binding of BMPs to their receptors is capable of producing an increase in the expression of Delta and/or Serrate. Such agents include Noggin, Chordin, Follistatin, FGFs, Fringe and derivatives and variants thereof.

The transgenic animal is typically a vertebrate, more preferably a rodent, such as a rat or a mouse, but also includes other mammals such as human, goat, pig or cow etc.

Such transgenic animals are useful as animal models of disease and in screening assays for new useful compounds. By specifically expressing one or more polypeptides, as defined above, the effect of such polypeptides on the development of disease can be studied. Furthermore, therapies including gene therapy and various drugs can be tested on transgenic animals. Methods for the production of transgenic animals are known in the art. For example, there are several possible routes for the introduction of genes into embryos. These include (i) direct transfection or retroviral infection of embryonic stem cells followed by introduction of these cells into an embryo at the blastocyst stage of development; (ii) retroviral infection of early embryos; and (iii) direct microinjection of DNA into zygotes or early embryo cells.

The present invention also includes stable cell lines for use as disease models for testing or treatment. A stable cell line will contain a recombinant gene or genes, also known herein as a transgene.

A cell line containing a transgene, as described herein, is made by introducing the transgene into a selected cell line according to one of several procedures known in the art for introducing a foreign gene into a cell.

The sequences encoding the inhibitors and enhancers of Notch-Notch ligand interactions as well as Notch or a Notch ligand itself are operably linked to control sequences, including promoters/enhancers and other expression regulation signals.

The promoter is typically selected from promoters which are functional in mammalian cells, although prokaryotic promoters and promoters functional in other eukaryotic cells may be used. The promoter is typically derived from promoter sequences of viral or eukaryotic genes. For example, it may be a promoter derived from the genome of a cell in which expression is to occur. With respect to eukaryotic promoters, they may be promoters that function in a ubiquitous manner (such as promoters of a-actin, b-actin, tubulin) or, alternatively, a tissue-specific manner (such as promoters of the genes for pyruvate kinase). Tissue-specific promoters specific for lymptocytes, dendritic cells, skin, brain cells and epithelial cells within the eye are particularly preferred, for example the CD2, CD11c, keratin 14, Wnt-1 and Rhodopsin promoters respectively. Preferably the epithelial cell promoter SPC is used. They may also be promoters that respond to specific stimuli, for example promoters that bind steroid hormone receptors. Viral promoters may also be used, for example the Moloney murine leukaemia virus long terminal repeat (MMLV LTR) promoter, the rous sarcoma virus (RSV) LTR promoter or the human cytomegalovirus (CMV) IE promoter.

It may also be advantageous for the promoters to be inducible so that the levels of expression of the heterologous gene can be regulated during the life-time of the cell. Inducible means that the levels of expression obtained using the promoter can be regulated.

In addition, any of these promoters may be modified by the addition of further regulatory sequences, for example enhancer sequences. Chimeric promoters may also be used comprising sequence elements from two or more different promoters described above.

Tumour Cells Expressing Notch Ligand

We have already identified expression of Notch ligands in melanoma cell lines. Other tumour cells may also be tested for expression of Notch ligands using a variety of techniques known in the art such as detection of mRNA by RT-PCR or detection of the Notch ligand polypeptides by Western blotting. Suitable tumour cells to be tested include cells present in malignancies such as cancer of the breast, cervix, colon, rectum, endometrium, kidney, lung, ovary, pancreas, prostate gland, skin, stomach, bladder, CNS, oesophagus, head-or-neck, liver, testis, thymus or thyroid. Malignant blood cells, bone marrow cells, B-lymphocytes, T-lymphocytes, lymphocytic progenitors or myeloid cell progenitors may also be tested.

The tumour cell to be tested for Notch ligand expression may be a tumour cell from a solid tumour or a non-solid tumour and may be a primary tumour cell or a disseminated metastatic (secondary) tumour cell. Non-solid tumours include myeloma; leukaemia (acute or chronic, lymphocytic or myelocytic) such as acute myeloblastic, acute promyelocytic, acute myelomonocytic, acute monocytic, erythroleukaemia; and lymphomas such as Hodgkin's, non-Hodgkin's and Burkitt's. Solid tumours include carcinoma, colon carcinoma, small cell lung carcinoma, non-small cell lung carcinoma, adenocarcinoma, melanoma, basal or squamous cell carcinoma, mesothelioma, adenocarcinoma, neuroblastoma, glioma, astrocytoma, medulloblastoma, retinoblastoma, sarcoma, osteosarcoma, rhabdomyosarcoma, fibrosarcoma, osteogenic sarcoma, hepatoma, and seminoma.

Antigen Presenting Cells and T Cells

Antigen-presenting cells (APCS) for use in the present invention may be "professional" antigen presenting cells or may be another cell that may be induced to present antigen to T cells. Alternatively a APC precursor may be used which differentiates or is activated under the conditions of culture to produce an APC. An APC for use in the ex vivo methods of the invention is typically isolated from a tumour or peripheral blood found within the body of a patient. Preferably the APC or precursor is of human origin. However, where APCs are used in preliminary in vitro screening procedures to identify and test suitable nucleic acid sequences, APCs from any suitable source, such as a healthy patient, may be used.

APCs include dendritic cells (DCs) such as interdigitating DCs or follicular DCs, Langerhans cells, PBMCs, macrophages, B-lymphocytes, T-lymphocytes, or other cell types such as epithelial cells, fibroblasts or endothelial cells, activated or engineered by transfection to express a MHC molecule (Class I or II) on their surfaces. Precursors of APCs include $CD34^+$ cells, monocytes, fibroblasts and endothelial cells. The APCs or precursors may be modified by the culture conditions or may be genetically modified, for instance by transfection of one or more genes encoding proteins which play a role in antigen presentation and/or in combination of selected cytokine genes which would promote to immune potentiation (for example IL-2, IL-12, IFN-γ, TNF-α, IL-18 etc.). Such proteins include MHC molecules (Class I or Class II), CD80, CD86, or CD40. Most preferably DCs or DC-precursors are included as a source of APCs.

Dendritic cells (DCs) can be isolated/prepared by a number of means, for example they can either be purified directly from peripheral blood, or generated from $CD34^+$ precursor cells for example after mobilisation into peripheral blood by treatment with GM-CSF, or directly from bone marrow. From peripheral blood, adherent precursors can be treated with a GM-CSF/IL-4 mixture (Inaba et al., 1992), or from bone marrow, non-adherent $CD34^+$ cells can be treated with GM-CSF and TNF-a (Caux et al., 1992). DCs can also be routinely prepared from the peripheral blood of human volunteers, similarly to the method of Sallusto and Lanzavecchia (1994) using purified peripheral blood mononucleocytes (PBMCs) and treating 2 hour adherent cells with GM-CSF and IL-4. If required, these may be depleted of $CD19^+$ B cells and $CD3^+$, $CD2^+$ T cells using magnetic beads (see Coffin et al., 1998). Culture conditions may include other cytokines such as GM-CSF or IL-4 for the maintenance and, or activity of the dendritic cells or other antigen presenting cells.

Where T cells are to be used in the ex vivo methods of the invention, the T cells are typically infiltrating T lymphocytes isolated from a solid tumour within the body of an individual suffering from a cancer. However, where T cells are used in preliminary in vitro screening procedures to identify and test suitable nucleic acid sequences, T cells from any suitable source, such as a healthy patient, may be used and may be obtained from blood or another source (such as lymph nodes, spleen, or bone marrow). They may optionally be enriched or purified by standard procedures. The T cells may be used in combination with other immune cells, obtained from the same or a different individual. Alternatively whole blood may be used or leukocyte enriched blood or purified white blood cells as a source of T cells and other cell types. It is particularly preferred to use helper T cells ($CD4^+$). Alternatively other T cells such as $CD8^+$ cells may be used. It may also be convenient to use cell lines such as T cell hybridomas.

Lymphocytes with antigen receptors recognising antigens presented by tumour cells (tumour-reactive lymphocytes (TRLs)) can be isolated from peripheral blood, lymph nodes or from tumour tissue (tumour-infiltrating lymphocytes (TILs)). Methods for isolating and culturing TRLs are well known in the art. See for example Vose et al. (1977). TILs and other TRLs may be isolated and expanded in culture in the presence of cytokines such as Interleukin (IL)-2, IL-12, IFN-γ, TNF-α, IL-18 as described by Belldegrun et al. (1988); Belldegrun et al. (1989); and Spiess et al. (1987). TRLs and TILs reactive with identified tumour antigens can also be isolated using MHC Class-I and Class-II tetramer technology (Dunbar et al., 1998; Romero et al, 1998).

Thus, it will be understood that the term "antigen presenting cell or the like" are used herein is not intended to be limited to APCs. The skilled man will understand that any vehicle capable of presenting to the T cell population may be used, for the sake of convenience the term APCs is used to refer to all these. As indicated above, preferred examples of suitable APCs include dendritic cells, L cells, hybridomas, fibroblasts, lymphomas, macrophages, B cells or synthetic APCs such as lipid membranes.

Introduction of Nucleic Acid Sequences into APCs, T Cells and Tumour Cells

T cells/APCs/tumour cells as described above are cultured in a suitable culture medium such as DMEM or other defined media, optionally in the presence of fetal calf serum. If required, a small aliquot of cells may be tested for down regulation of Notch ligand expression as described above. Alternatively, cell activity may be measured by the inhibition of T-cell proliferation as described in WO98/20142. T-cells/APCs/tumour cells transfected with a nucleic acid construct directing the expression of, for example Serrate, may be used as a control.

As discussed above, polypeptide substances may be administered to T cells/APCs/tumour cells by introducing nucleic acid constructs/viral vectors encoding the polypeptide into cells under conditions that allow for expression of the polypeptide in the T cell/APC/tumour cell. Similarly, nucleic acid constructs encoding antisense constructs may be introduced into the T cells/APCs/tumour cells by transfection, viral infection or viral transduction.

The resulting T cells/APCs/tumour cell that comprise nucleic acid constructs capable of downregulating Notch ligand expression are now ready for use. For example, they may be prepared for administration to a patient or incubated with T cells in vitro (ex vivo).

Exposure of Agent to APCs and T Cells

T cells/APCs/tumour cells may be cultured as described above. The APCs/T cells/tumour cells may be incubated/exposed to substances which are capable of interferring with or downregulating Notch or Notch ligand expression. The resulting T cells/APCs/tumour cells that have downregulated Notch or Notch ligand expression are now ready for use. For example, they may be prepared for administration to a patient or incubated with T cells in vitro (ex vivo).

For example, tumour material may be isolated and transfected with a nucleic acid sequence which encodes for, e.g., a Toll-like receptor or BMP receptor and/or costimulatory molecules (suitable costimulants are mentioned above) and/or treated with cytokines, e.g. IFN-γ, TNF-α, IL-12, and then used in vitro to prime TRL and/or TIL cells.

Therapeutic Uses

The T cells/APCs/tumour cells prepared by the method of the invention may be administered to a patient suffering from a malignancy, the malignancy typically comprising cancerous cells that express a Notch ligand. The presence of cancerous cells that express, in particular over-express, a Notch ligand may be determined by, for example, testing using the methods described above a sample of cancerous tissue obtained from the patient.

Generally, the patient will be the same patient from whom the treated T cells/APCs/tumour cells originated. Examples of malignancies that may be treated include cancer of the breast, cervix, colon, rectum, endometrium, kidney, lung, ovary, pancreas, prostate gland, skin, stomach, bladder, CNS, oesophagus, head-or-neck, liver, testis, thymus or thyroid. Malignancies of blood cells, bone marrow cells, B-lymphocytes, T-lymphocytes, lymphocytic progenitors or myeloid cell progenitors may also be treated.

The tumour may be a solid tumour or a non-solid tumour and may be a primary tumour or a disseminated metastatic (secondary) tumour. Non-solid tumours include myeloma; leukaemia (acute or chronic, lymphocytic or myelocytic) such as acute myeloblastic, acute promyelocytic, acute myclomonocytic, acute monocytic, erythroleukaemia; and lymphomas such as Hodgkin's, non-Hodgkin's and Burkitt's. Solid tumours include carcinoma, colon carcinoma, small cell lung carcinoma, non-small cell lung carcinoma, adenocarcinoma, melanoma, basal or squamous cell carcinoma, mesothelioma, adenocarcinoma, neuroblastoma, glioma, astrocytoma, medulloblastoma, retinoblastoma, sarcoma, osteosarcoma, rhabdomyosarcoma, fibrosarcoma, osteogenic sarcoma, hepatoma, and seminoma.

The tumour may be one which presents intracellular or membrane-bound antigens including tumour-specific antigens (for example virally encoded antigens, neo-antigens such as MUC1, antibody idiotypes); antigens which are over-expressed on the surface of tumour cells; oncofoetal antigens including cancer-testis (CT) antigens; or differentiation-antigens (such as tyrosinase and melanocyte antigens). The patient may have an ongoing immune response, such as a Th1 or Th2-type immune response, to antigens on the tumour and may have detectable cytotoxic T cell (CTL) activity, NK cell activity and/or antibody responses against the tumour as determined by, for example, in vitro assays.

Tumour Antigens and Antigenic Determinants

In one embodiment, the agent may be administered simultaneously, separately or sequentially with a tumor antigen for the immunotherapeutic treatment of cancers.

The term "tumor antigen" includes a molecule or complex which is expressed at a higher frequency or density by tumor cells than by non-tumor cells of the same tissue type. Tumor-associated antigens may be antigens not normally expressed by the host; they may be mutated, truncated, misfolded, or otherwise abnormal manifestations of molecules normally expressed by the host; they may be identical to molecules normally expressed but expressed at abnormally high levels; or they may be expressed in a context or milieu that is abnormal. Tumor-associated antigens may be, for example, proteins or protein fragments, complex carbohydrates, gangliosides, haptens, nucleic acids, or any combination of these or other biological molecules.

Suitable antigens include those associated with prostrate, breast, colorectal, lung, pancreatic, renal or melanoma cancers. Examples of antigens include, for example MAGE 1 and MAGE 3 or other MAGE antigens for the treatment of melanoma, PRAME, BAGE or GAGE (Robbins and Kawakami, 1996, Current Opinions in Immunology 8, pps 628-636; Van den Eynde et al., International Journal of Clinical & Laboratory Research (submitted 1997); Correale et al. (1997), Journal of the National Cancer Institute 89, p293). These antigens are expressed in a wide range of tumor types such as melanoma, lung carcinoma, sarcoma and bladder carcinoma. Other Tumor-Specific antigens are suitable for use with the present invention and include, but are not restricted to Prostate specific antigen (PSA) or Her-2/neu, KSA (GA733), MUC-1 and carcinoembryonic antigen (CEA).

Tumor-associated antigens which may be used in such a method include, for example:

beta chain of human chorionic gonadotropin (hCG beta) antigen, carcinoembryonic antigen, EGFRvIII antigen, Globo H antigen, GM2 antigen, GP100 antigen, HER2/neu antigen, KSA antigen, Le (y) antigen, MUCI antigen, MAGE 1 antigen, MAGE 2 antigen, MUC2 antigen, MUC3 antigen, MUC4 antigen, MUC5AC antigen, MUC5B antigen, MUC7 antigen, PSA antigen, PSCA antigen, PSMA antigen, Thompson-Friedenreich antigen (TF), Tn antigen, sTn antigen, TRP 1 antigen, TRP 2 antigen, tumor-specific immunoglobulin variable region and tyrosinase antigen.

Pharmaceutical Compositions

The agents used in the present invention will usually be administered in the form of a pharmaceutical composition comprising a therapeutically effective amount of an agent in accordance with the present invention and a pharmaceutically acceptable carrier, diluent or excipients (including combinations thereof).

The pharmaceutical compositions may be for human or animal usage in human and veterinary medicine and will typically comprise any one or more of a pharmaceutically acceptable diluent, carrier or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be delivered using a minipump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be delivered by both routes.

Where the compound is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Administration

APCs/T cells/tumour cells prepared by the methods of the present invention for use in immunotherapy are typically formulated for administration to patients with a pharmaceutically acceptable carrier or diluent to produce a pharmaceutical composition. Suitable carriers and diluents include isotonic saline solutions, for example phosphate-buffered saline. The composition may be formulated for parenteral, intramuscular, intravenous, intra-peritoneal, injection, intranasal inhalation, lung inhalation, intradermal, intra-articular, intrathecal, or via the alimentary tract (for example, via the Peyers patches).

Typically, a physician will determine the actual dosage which will be most suitable for an individual subject and it will vary with the age, weight and response of the particular patient. The dosages below are exemplary of the average case. There can, of course, be individual instances where higher or lower dosage ranges are merited.

The compositions of the present invention may be administered by direct injection. The composition may be formulated for parenteral, mucosal, intramuscular, intravenous, subcutaneous, intraocular or transdermal administration.

The term "administered" includes delivery by viral or non-viral techniques. Viral delivery mechanisms include but are not limited to adenoviral vectors, adeno-associated viral (AAV) vectos, herpes viral vectors, retroviral vectors, lentiviral vectors, and baculoviral vectors. Non-viral delivery mechanisms include lipid mediated transfection, liposomes, immunoliposomes, lipofectin, cationic facial amphiphiles (CFAs) and combinations thereof. The routes for such delivery mechanisms include but are not limited to mucosal, nasal, oral, parenteral, gastrointestinal, topical, or sublingual routes.

The term "administered" includes but is not limited to delivery by a mucosal route, for example, as a nasal spray or aerosol for inhalation or as an ingestable solution; a parenteral route where delivery is by an injectable form, such as, for example, an intravenous, intramuscular, intradermal, intra-articular, intrathecal, intra-peritoneal or subcutaneous route, or via the alimentary tract (for example, via the Peyers patches).

Cells and pharmaceutical compositions comprising cells produced by the methods of the invention are typically administered to the patient by intramuscular, intraperitoneal or intravenous injection, or by direct injection into the lymph nodes of the patient, preferably by direct injection into the lymph nodes. Typically from $10^4$ to $10^8$ treated cells, preferably from $10^5$ to $10^7$ cells, more preferably about $10^6$ cells are administered to the patient.

The routes of administration and dosages described are intended only as a guide since a skilled practitioner will be able to determine readily the optimum route of administration and dosage for any particular patient depending on, for example, the age, weight and condition of the patient. Preferably the pharmaceutical compositions are in unit dosage form. The present invention includes both human and veterinary applications.

Figure 2:
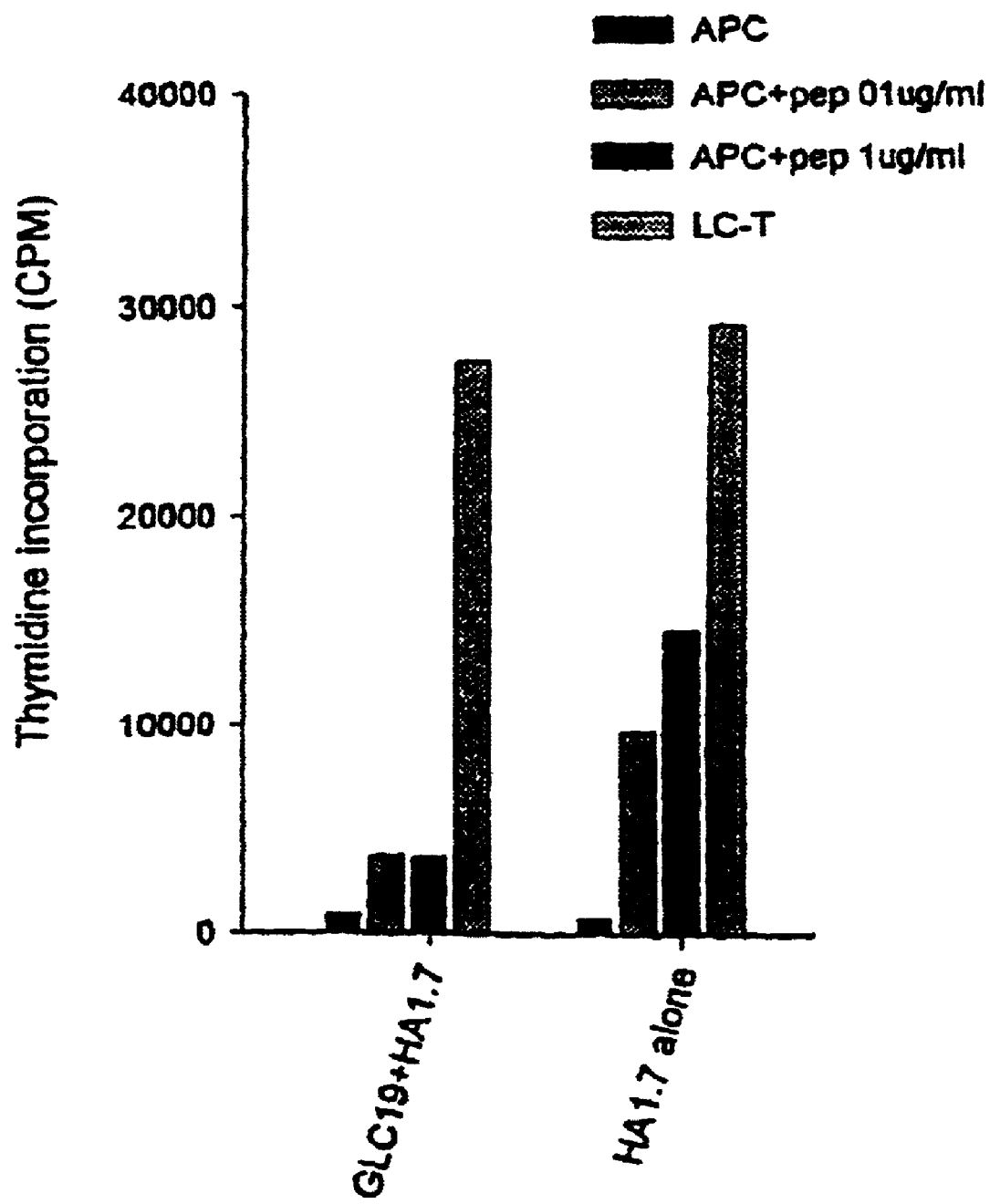

The present invention will now be described by way of examples which are intended to be illustrative only and non-limiting, and with reference to the accompanying drawings in which:

FIG. 1 shows expression of Notch receptors and Notch ligands in lung tumours; and FIG. 2 shows a graph illustrating co-culture of human CD4+ T cells (HA1.7) with the SCLC line (GLC-19) renders them unresponsive to antigenic restimulation.

EXAMPLES

Example 1

Small Cell Lung Tumour Cells Express Components of the Notch Signalling Pathway

Small cell lung tumour cell (SCLC) lines (GLC-19, NCI-H69, NCI-H345, NCI-H711, Lu-165, COR-L24 and COR-L188) and non-small cell lung tumour cell (NSCLC) lines (NCI-H460, MOR/P, COR-L23 and A549) were grown in culture medium (RPMI-1640) supplemented with 10% foetal calf serum in tissue culture flasks and maintained at a density of $2-5\times10^6$ cells per ml. Cells were collected and centrifuged at 1500 rpm resuspended in lysis buffer and total RNA extracted. RNA is prepared from cell pellets by homogenisation in guanidium thiocyanate solution followed by CsCl density centrifugation.

RT-PCR was performed using an Access RT-PCR kit (Promega). One μg of total RNA was used in each reaction together with specific oligonucleotide primers (50 pmol) for the following human genes—Delta1, Jagged (Serrate) 1 and 2, hASH-1, Notch 1, 2 and 3, Radical fringe (controls actin and GAPDH)—and murine genes Hes-1 and Hes-5 under conditions according to the manufacturer's instructions. PCR was performed using a Hybaid machine, dynazyme II polymerase, 1.5 mM $Mg^{2+}$, 28-35 cycles at an annealing temperature of 60° C.

The sequences of the primers are as follows:

```
Delta (accession number AF003522)
forward primer    5'-TTTTCTGCAACCAGGACCTGAAC-3'
                  (SEQ ID NO:1)

reverse primer    5'-CACACACTTGGCACCATTAGAAC-3'
                  (SEQ ID NO:2)

Jagged 1 (Serrate 1) (accession number U73936):
forward primer    5'-TGACAAATATCAGTGTTCCTGCCC-3'
                  (SEQ ID NO:3)

reverse primer    5'-AGCGATAACCATTAACCAAATCCC-3'
                  (SEQ ID NO:4)

Jagged 2 (Serrate2) (accession number AF029778):
forward primer    5'-TGGGACTGGGACAACGATAC-3'
                  (SEQ ID NO:5)

reverse primer    5'-GCAAATTACACCCTTGTTTACACA-3'
                  (SEQ ID NO:6)

Hes-1 (accession number mouse D16464):
forward primer    5'-AATGGAGAATTCCTCCTCCC-3'
                  (SEQ ID NO:7)

reverse primer    5'-TCACCTCGTTCATGCACTCG-3'
                  (SEQ ID NO:8)

Hes-5 (accession number mouse D32132):
forward primer    5'-AAGGAGAAAAACCGACTG-3'
                  (SEQ ID NO:9)

reverse printer   5'-TGTGTTTCAGGTAGCTGAC-3'
                  (SEQ ID NO:10)

hASH-1 (accession number L08424):
forward primer    5'-AACAAGAAGATGAGTAAGGTGGAG-3'
                  (SEQ ID NO:11)

reverse primer    5'-TGGAGTTCAAGTCGTTGGAGTAG-3'
                  (SEQ ID NO:12)

Notch 1 (accession number M73980):
forward primer    5'-GCCAGAACTGTGAGGAAAATATCG-3'
                  (SEQ ID NO:13)

reverse primer    5'-CAGATGGCCTTGCCATTGAC-3'
                  (SEQ ID NO:14)

Notch 2 (accession number X80115):
forward primer    5'-TAACTCCTTCTCTTGCTTGTGCC-3'
                  (SEQ ID NO:15)

reverse primer    5'-ACACACTCGCATCTGTATCCACC-3'
                  (SEQ ID NO:16)
```

-continued

```
Notch 3 (accession number NM-000435):
forward primer:   5'-TAGGAGGGAGAAGCCAAGTC-3'
                  (SEQ ID NO:17)

reverse primer    5'-AAAAAGGCAATAGGCCCCAG-3'
                  (SEQ ID NO:18)

Radical fringe (accession number AF108139):
forward primer    5'-ATGACAATTATGTGAACGCAAGGA-3'
                  (SEQ ID NO:19)

reverse primer    5'-ACCAGTAGCAAACCAGAACTTGAC-3'
                  (SEQ ID NO:20)
```

PCR samples were analysed by gel electrophoresis.

The results (FIG. 1) demonstrate that SCLC express transcripts for:
Delta1 except for NCI-H345
Jagged1 (Serrate1) except for NCI-H345
Jagged2 (Serrate2) except for GLC-19, NCI-H69, NCI-H345 and NCI-H711
Hes-1
Hes-5 except for GLC 19
hASH-1
Notch2, Notch3 and Radical fringe
All are negative for Notch 1

Expression of transcripts for these components of the Notch signalling pathway was also analysed for NSCLC lines (FIG. 1) and most notably none of them expressed Delta1.

Example 2

Induction of Unresponsiveness in Human T Cells Following Interaction with SCLC Cells Cloned human CD4+ T cells (HA1.7), as described in Lamb et al. (1983), were cultured at $2 \times 10^6$ cells per well in 12 well tissue culture plates together with irradiated (6000 rads) SCLC (GLC19) at 0.5×10 per well for 24 hours or alone in tissue culture medium (RPMI-1640 supplemented with 10% human A+ serum).

The T cells were then restimulated with irradiated (6000 rads) autologous EBV transformed B cells ($2.5 \times 10^4$ per well, as a source of antigen presenting cells) together with increasing concentrations of cognate peptide (influenza) virus haemagglutinin residues 306-318, at 0.1 or 1 μg/ml) or in Interleukin 2 (IL-2; 10% v/v) alone in 96 well tissue culture plates. The cell cultures were pulsed with tritiated thymidine (3[H]-TdR, 0.1 μCi per well) and harvested 72 hours after the initiation of the cultures. The incorporation of 3[H]-TdR as a measure of T cell proliferation was determined by liquid scintillation chromatography.

The T cells (HA1.7) failed to respond to antigen restimulation but were able to proliferate in the presence of exogenous IL-2 demonstrating that the inhibitory effects of the SCLC was not due to cytolytic activity (FIG. 2).

The results indicate that the interaction between human CD4+ T cells and SCLC can render the T cells unresponsive to restimulation with specific antigen.

Example 3

The Serrate-1 Gene is Expressed in Melanoma Cell Lines

Mouse melanoma cell lines MC57 and B16F10 were cultured in RPMI-1640 medium with 10% FCS at 37° C. Cells were collected and centrifuged at 1500 rpm, resuspended in lysis buffer and total RNA extracted.

RT-PCR was performed using an Access RT-PCR kit (Promega). 50 ng RNA was used in each reaction together with Serrate-1 gene specific oligonucleotide primers (50 pmol) under conditions according to the manufacturer's instructions ($T_m$ for the Serrate oligonucleotides=58° C.).

The sequence of the "forward" Serrate-1 primer is:

The sequence of the "forward" Serrate-1 primer is:
(SEQ ID NO:21)
5'-GGCTGGGAAGGAACAACCTG-3'

The Serrate-1 "reverse" primer is:
(SEQ ID NO:22)
5'-GGTAGCCATTGATCTCATCCAC-3'

Primers specific for Delta are:
(SEQ ID NO:23)
5'-GATTCTCCTGATGACCTCGC-3' and (SEQ ID NO:24)
5'-GTGTTC GTCACACACGAAGC-3'

A PCR-product of the predicted size (330 bp) was observed from RNA obtained from each of the two melanoma cell lines. No Delta-specific PCR product was detected.

These results show that melanoma cell lines express Serrate-1 but not detectable levels of Delta RNA.

REFERENCES

Belldegrun et al. (1988) Cancer Res. 48: 206-214
Belldegrun et al. (1989) J. Immunol. 134: 4520-4526
Caux C, et al. (1992) Nature 360: 258-261
Coffin R S, et al. (1998) Gene Therapy 5: 718-722
Dkuz et al. (1997) Cell 90:271-280
Dunbar et al. (1998) Curr. Biol. 8: 413-416
Eddison et al. (2000) Proc. Natl. Acad. Sci. 97(22): 11692-9
Hemmati-Brivanlou and Melton (1997) Cell 88: 13-17
Iemura et al. (1998) PNAS 95: 9337-9342
Inaba K, et al. (1992) J. Exp. Med. 175: 1157-1167
Lamb et al. (1983) J. Exp. Med. 157: 1434-1447
Lee et al. (2000) Curr. Biol. 10(15): 931-4
Li et al. (1998) Immunity 8(1):43-55
Medhzhitov et al. (1997) Nature 388: 394-397
Romero et al. (1998) J. Exp. Med. 188: 1641-1650)
Sallusto F and Lanzavecchia A (1994) J. Exp. Med. 179: 1109-1118
Sasai et al. (1994) Cell 79: 779-790
Spiess et al. (1987) J. Nat. Cancer Inst. 79: 1067-1075
Takahashi et al. (2000) Nat. Genet. 25(4): 390-6
Valenzuela et al. (1995) J. Neurosci 15: 6077-6084
Vose et al. (1977) Eur. J. Immunol. 7: 353-357
Wilson and Hemmati-Brivanlou (1997) Neuron 18: 699-710
Zhao et al. (1995) J. Immunol 155:3904-3911.

The invention claimed is:

1. A method of treating a tumour by reducing or preventing interaction between Notch and an endogenous Notch ligand in a patient in need thereof, comprising the steps of:
   (a) administering a tumour antigen expressed by the tumour to a patient; and
   (b) exposing the patient to an agent, wherein the agent is capable of reducing or preventing interaction between Notch and an endogenous Notch ligand, and wherein the agent is a polypeptide having a DSL domain at the N-terminus and 3 to 8 EGF-like repeats wherein the polypeptide does not activate Notch.

2. The method according to claim 1, wherein the tumour antigen is administered topically to the skin of the patient.

3. The method according to claim 1, wherein the tumour is a melanoma.

4. The method according to claim 1, wherein the tumour is a small cell lung tumour.

5. The method according to claim 1, wherein the polypeptide is selected from the group consisting of derivatives of Serrate, Delta and homologues thereof.

6. The method according to claim 1, wherein the agent is selected from the group consisting of derivatives of Serrate and Delta.

7. The method according to claim 1, wherein the agent is a peptide comprising the Delta/Serrate/LAG-2 domain of h-Jagged1.

8. The method according to claim 1, wherein the agent is a soluble form of the extracellular portion of h-Jagged1.

9. The method of claim 1 wherein the tumour is cancer of the breast, cervix, colon, rectum, endometrium, kidney, lung, ovary, pancreas, prostate gland, skin, stomach, bladder, CNS, oesophagus, head-or-neck, liver, testis, thymus or thyroid.

10. The method of claim 1 wherein the tumour is a non-solid tumour selected from myeloma, leukaemia or lymphoma.

11. The method of claim 1 wherein the tumour is a solid tumour selected from carcinoma, colon carcinoma, non-small cell lung carcinoma, adenocarcinoma, basal or squamous cell carcinoma, mesothelioma, adenocarcinoma, neuroblastoma, glioma, astrocytoma, medulloblastoma, retinoblastoma, sarcoma, osteosarcoma, rhabdomyosarcoma, fibrosarcoma, osteogenic sarcoma, hepatoma or seminoma.

12. The method of claim 1 wherein the polypeptide comprises a DSL domain from human Delta at the N-terminus and 3 to 8 EGF-like repeats from human Delta.

* * * * *